(12) United States Patent
Plamondon et al.

(10) Patent No.: US 12,257,088 B2
(45) Date of Patent: Mar. 25, 2025

(54) ESTIMATING SCATTER IN X-RAY IMAGES CAUSED BY IMAGING SYSTEM COMPONENTS USING SPATIALLY-DEPENDENT KERNELS

(71) Applicant: SIEMENS HEALTHINEERS INTERNATIONAL AG, Palo Alto, CA (US)

(72) Inventors: Mathieu Plamondon, Glattbrugg (CH); Balazs Nagy, Schlieren (CH); Mathias Lehmann, Zürich (CH); Adam Michal Strzelecki, Daettwil (CH); Igor Peterlik, Kuenten AG (CH); Dieter Marc Seghers, Zürich (CH)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 82 days.

(21) Appl. No.: 17/970,741

(22) Filed: Oct. 21, 2022

(65) Prior Publication Data

US 2024/0130699 A1 Apr. 25, 2024
US 2024/0225572 A9 Jul. 11, 2024

(51) Int. Cl.
*A61B 6/03* (2006.01)
*A61B 6/06* (2006.01)
*A61B 6/40* (2024.01)

(52) U.S. Cl.
CPC .................. *A61B 6/40* (2013.01); *A61B 6/03* (2013.01); *A61B 6/06* (2013.01); *G01N 2223/419* (2013.01)

(58) Field of Classification Search
CPC .... A61B 6/40; A61B 6/03; A61B 6/06; G01N 2223/419; G06T 2211/452; G06T 11/005;
(Continued)

(56) References Cited

U.S. PATENT DOCUMENTS 8,055,052 B2 * 11/2011 Burns ....................... G06T 5/70
382/128
8,625,107 B2 1/2014 Kusik et al.
(Continued)

FOREIGN PATENT DOCUMENTS

CN 108065950 A 5/2018
CN 109646026 A 4/2019
WO 03/073377 A2 9/2003

OTHER PUBLICATIONS

M Sun et al, "Improved scatter correction using adaptive scatter kernel superposition", Physic in Medicine and Biology, 2010, pp. 6695-6720, vol. 55.
(Continued)

*Primary Examiner* — Courtney D Thomas
(74) *Attorney, Agent, or Firm* — SU IP CONSULTING

(57) ABSTRACT

A computer-implemented method of reducing scatter in an X-ray projection image of an object comprises: generating an initial X-ray projection image with an imaging beam and an X-ray detector; based on a first position in a detector array of the X-ray detector, selecting a first kernel for convolution of a first portion of the initial projection image, wherein the first position corresponds to the first portion of the initial projection image; based on a second position in the detector array of the X-ray detector, selecting a second kernel for convolution of a second portion of the initial projection image, wherein the second position corresponds to the second portion of the initial projection image; convolving the first portion with the first kernel and the second portion with the second kernel to generate a scatter component of the initial X-ray projection image; and generating a corrected X-ray projection image by removing the scatter component from the initial X-ray projection image.

20 Claims, 11 Drawing Sheets

(58) Field of Classification Search
CPC . G06T 2207/10081; G06T 2207/10116; G06T 5/73
See application file for complete search history.

(56) References Cited

U.S. PATENT DOCUMENTS

| | | |
|---|---|---|
| 2006/0115054 A1 | 6/2006 | Yatsenko et al. |
| 2009/0290682 A1 | 11/2009 | Star-Lack et al. |
| 2011/0255656 A1 | 10/2011 | Star-Lack et al. |
| 2012/0207370 A1 | 8/2012 | Fahimian et al. |
| 2012/0236983 A1 | 9/2012 | Star-Lack et al. |
| 2012/0263360 A1 | 10/2012 | Zhu et al. |
| 2015/0371414 A1 | 12/2015 | Choi et al. |
| 2016/0093030 A1 | 3/2016 | Naito et al. |
| 2016/0213345 A1 | 7/2016 | Star-Lack et al. |
| 2017/0055933 A1 | 3/2017 | Kawamura |
| 2018/0061031 A1 | 3/2018 | Rong et al. |
| 2018/0268573 A1 | 9/2018 | Fukuda |
| 2018/0279977 A1 | 10/2018 | Shinden |
| 2018/0330233 A1 | 11/2018 | Rui et al. |
| 2019/0197740 A1 | 6/2019 | Lu et al. |
| 2020/0170601 A1 | 6/2020 | Gagnon et al. |
| 2020/0174144 A1 | 6/2020 | Yamakawa |
| 2020/0234471 A1 | 7/2020 | Lu et al. |
| 2024/0130700 A1 | 4/2024 | Plamondon et al. |

OTHER PUBLICATIONS

Alexander Maslowski et al., "Acuros CTS: A fast, linear Boltzmann transport equation solver for computed tomography scatter—Part I: Core algorithms and validation", Medical Physics, May 2018, pp. 1899-1913, vol. 45, No. 5.

Adam Want et al., Acuros CTS: A fast, linear Boltzmann transport equation solver for computed tomography scatter—Part II: System modeling, scatter correction, and optimization, Medical Physics, May 2018, pp. 1914-1925, vol. 45, No. 5.

Machine translation of CN-109646026 (CN patent document submitted on Apr. 25, 2024).

* cited by examiner

ESTIMATING SCATTER IN X-RAY IMAGES CAUSED BY IMAGING SYSTEM COMPONENTS USING SPATIALLY-DEPENDENT KERNELS

CROSS-REFERENCE TO RELATED APPLICATION

The present application is related in subject matter to U.S. patent application Ser. No. 17/970,744, which is incorporated herein by reference.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area, referred to as the "treatment planning image." From such imaging, the size and mass of the target tissue can be estimated, a planning target volume determined, and an appropriate treatment plan generated.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues immediately before and/or while radiation treatment is delivered to the planning target volume. IGRT incorporates imaging coordinates from the treatment plan to ensure the patient is properly aligned for treatment in the radiation therapy device. Generally, the target tissues are viewed using a reconstructed region of patient anatomy that is generated based on X-ray images of the region.

For reconstruction of patient anatomy surrounding a planning target volume, computed tomography (CT) or cone-beam computed tomography (CBCT) is often employed for generating the two-dimensional (2D) projections images from which the patient anatomy is reconstructed. In such image reconstruction, the quality of images generated from the reconstructed anatomical region can be negatively impacted by various sources of visual artifacts. These visual artifacts can be caused by metal objects and high-density tissues within the scanned anatomical region and/or by various sources of X-ray scatter. For example, X-ray scatter can cause severe streaking and cupping artifacts in 2D projection images, thereby degrading image quality and reducing the accuracy of a reconstructed anatomical region. Further, the addition of X-ray scatter to CBCT images can introduce errors in CT values and increase noise in a reconstructed anatomical region. Consequently, many approaches have been studied for the correction of X-ray scatter in CBCT image acquisition. Despite such efforts, the degradation of CBCT 2D projection images by X-ray scatter continues to be a significant problem.

In light of the above, there is a need in the art for improved scatter correction techniques for CBCT images.

SUMMARY

According to various embodiments, X-ray scatter that is included in a 2D projection image of an object is estimated and removed from the 2D projection image to produce a corrected image of the object. In some embodiments, a model-based correction is employed to estimate the scatter signal contributed by an individual scatter source to the X-ray scatter included in the projection image. Further, in some embodiments, a different model-based correction is employed to estimate the scatter signal contributed by each of the scatter sources. Generally, each individual scatter source is associated with a different specific component of an imaging system that is used to generate the 2D projection image, such as off-focal radiation generated at an anode of the imaging system, elements of the X-ray source that contribute to inherent filtration (e.g., a tube glass, an insert window, dielectric oil, and/or a front window of the X-ray source), beam shaping elements of the imaging system (bow-tie and filters), beam collimation of the imaging system (diaphragm associated with the X-ray source, precollimator and collimator blades), covers of the imaging system that are disposed between the X-ray source and the object (bore and source covers), covers of the imaging system that are disposed between the object and an X-ray detector (bore and detector covers), and/or one or more components of the X-ray detector of the imaging system.

In some embodiments, a computer-implemented method of reducing scatter in an X-ray projection image of an object comprises: generating an initial X-ray projection image with an imaging beam and an X-ray detector; based on a first position in a detector array of the X-ray detector, selecting a first kernel for convolution of a first portion of the initial projection image, wherein the first position corresponds to the first portion of the initial projection image; based on a second position in the detector array of the X-ray detector, selecting a second kernel for convolution of a second portion of the initial projection image, wherein the second position corresponds to the second portion of the initial projection image; convolving the first portion with the first kernel and the second portion with the second kernel to generate a scatter component of the initial X-ray projection image; and generating a corrected X-ray projection image by removing the scatter component from the initial X-ray projection image.

In some embodiments, a computer-implemented method of reducing scatter in an X-ray projection image of an object, the method comprising: generating an initial X-ray projection image of an object with an imaging beam produced by an imaging system; based on a first transmission indicator for the object and on a second transmission indicator for at least one element of the imaging system, selecting a kernel for convolution of the initial projection image; convolving the initial X-ray projection image with the kernel to generate a scatter component of the initial X-ray projection image; and generating a corrected X-ray projection image by removing the scatter component from the initial X-ray projection image.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
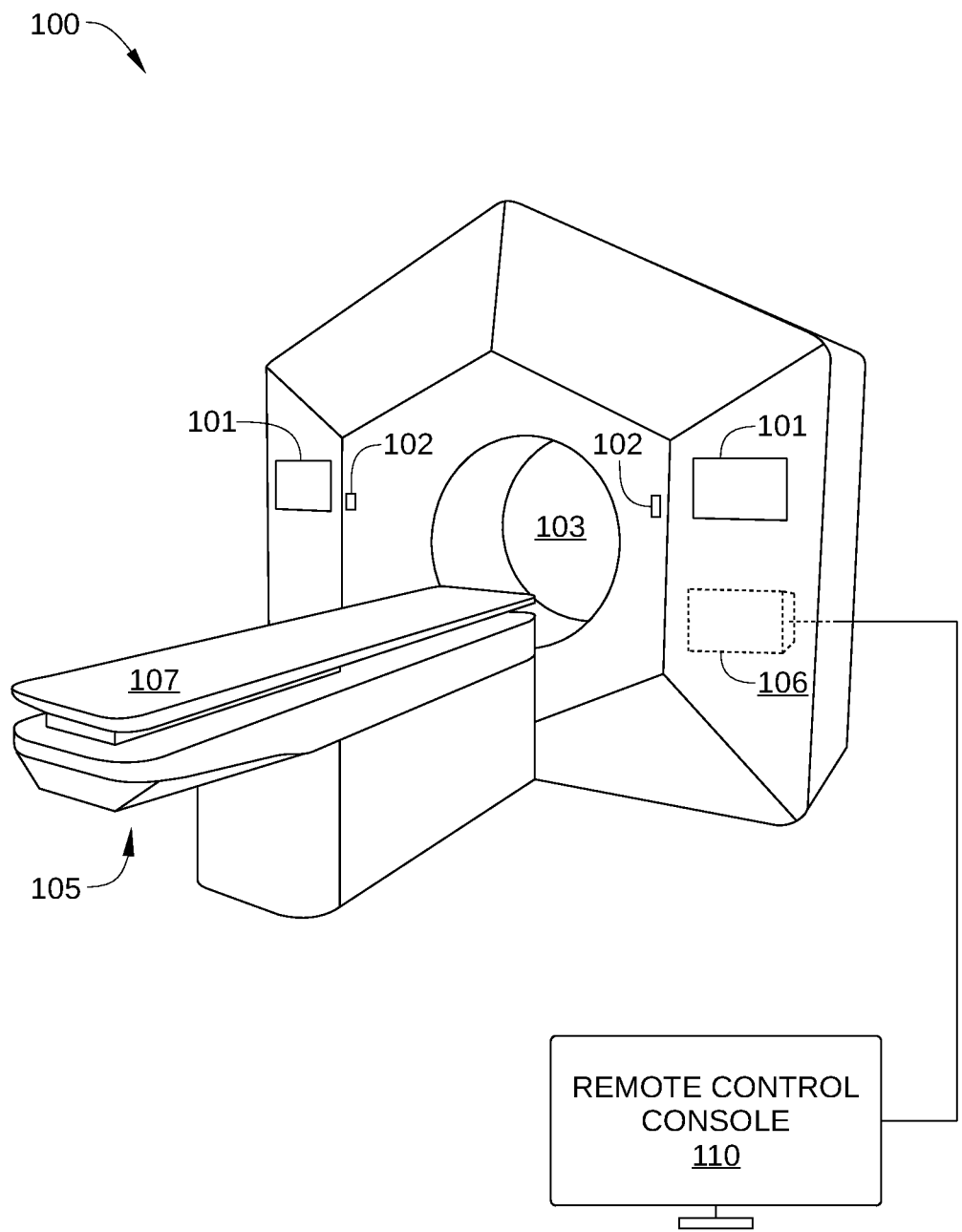
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

As noted previously, X-ray scatter that occurs during acquisition of CBCT projection images can cause visual artifacts in the CBCT projection images. These visual artifacts generally degrade the quality of an anatomical region that is reconstructed based on the CBCT projection images, and therefore can impact the ability to accurately detect the current location of a target volume and/or critical structures proximate to a target volume within the anatomical region. In many instances, hardware components of the imaging system that acquires the 2D projection image can produce such X-ray scatter. Similar to X-ray scatter generated by the patient or object being imaged, X-ray scatter caused by hardware components can impinge on the X-ray detector of the imaging system and contribute unwanted noise, or "scatter signal," to the 2D projection image. As a result, the quality of CBCT-acquired 2D projection images is usually degraded by hardware-related scatter, causing loss of contrast and sharpness as well as shadings. Techniques for correcting X-ray scatter generated by the patient or object being imaged has been studied extensively. By contrast, the X-ray scatter caused by specific hardware components of an imaging system are generally ignored in most reconstruction algorithms, which prevents a region of patient anatomy (or other object being scanned) from being reconstructed with optimal accuracy.

According to various embodiments, a model-based correction is employed for the scatter signal contributed by an individual hardware-related scatter source to a 2D projection image. Further, in some embodiments, a plurality of such scatter corrections are performed, where the contribution of each different hardware-related scatter source is determined via a different model-based correction. In the embodiments, the correction of an acquired projection image for each hardware-related scatter source involves the convolution of a set of model-based physics kernels with the acquired projection image to generate a scatter component. The correction of the acquired projection image further involves the subtraction of the scatter component from the acquired projection image. Thus, the contribution of each hardware-related scatter source to an acquired projection image can be corrected for individually. Various example embodiments are described below.

System Overview

FIG. 1 is a perspective view of a radiation therapy system 100 that can beneficially implement various embodiments. In some embodiments, radiation therapy (RT) system 100 includes an imaging system configured to detect intra-fraction motion in near-real time using X-ray imaging techniques. Thus, in such embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection. In yet other embodiments, any imaging system capable of generating 2D projection X-ray images, for example as part of a CBCT process, can beneficially implement the various embodiments described herein.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
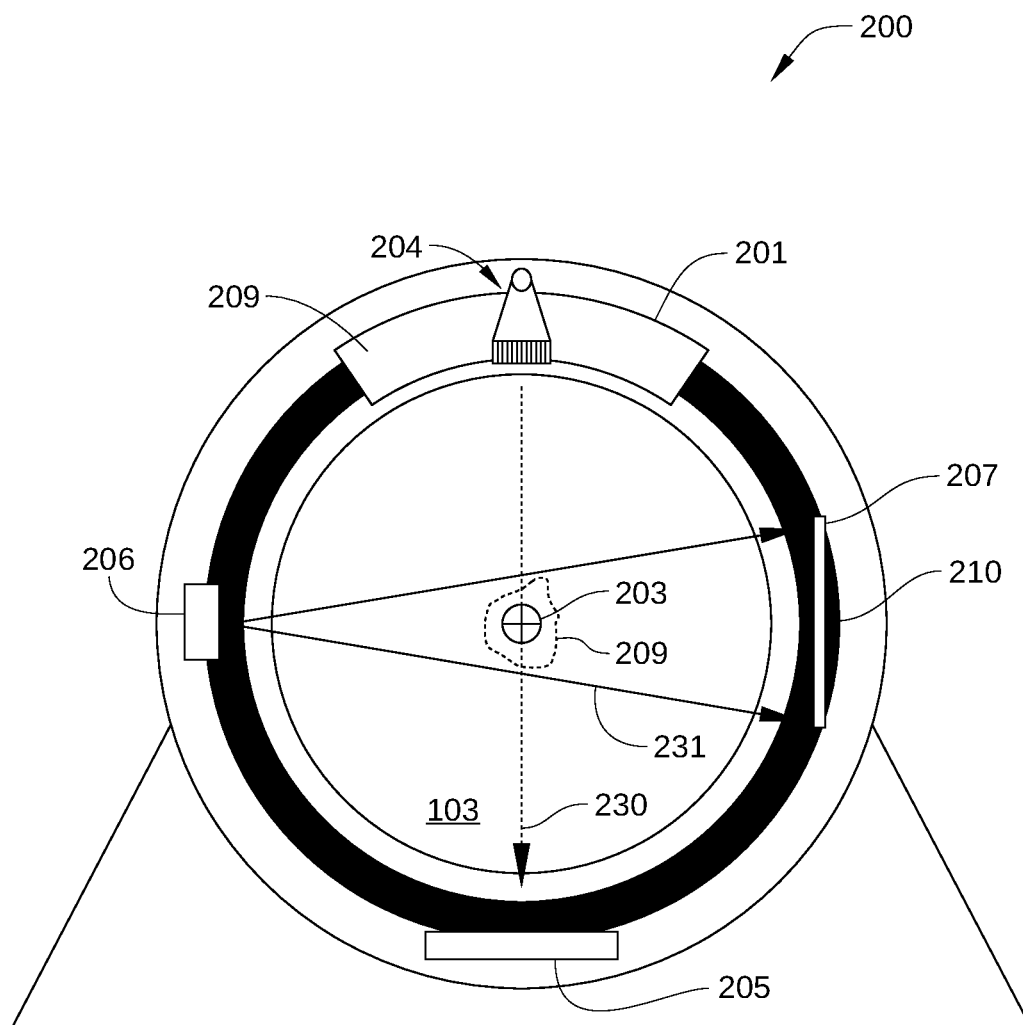
FIG. 2 schematically illustrates a drive stand and gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
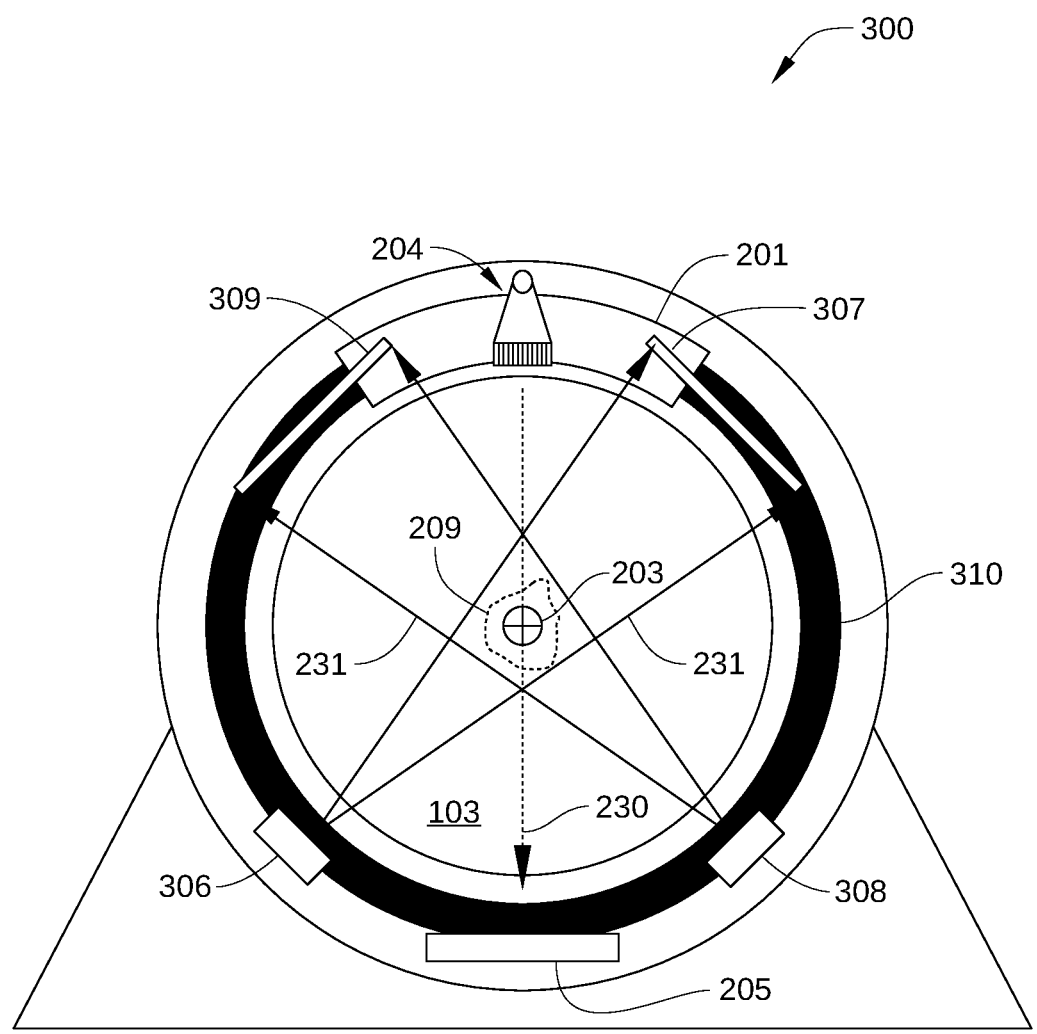
FIG. 3 schematically illustrates a drive stand and a gantry of the radiation therapy system of FIG. 1, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 200 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 in FIG. 2 (or by first x-ray imager 307 and second X-ray imager 309 in FIG. 3) are used to construct imaging data for a 3D digital volume of an object or portion of patient anatomy, such as a 3D region of patient anatomy that includes a target volume. Alternatively or additionally, such projection images can be used to update portions of existing imaging data for the digital volume corresponding to the 3D region. One embodiment of such a digital volume is described below in conjunction with FIG. 4.

Figure 4:
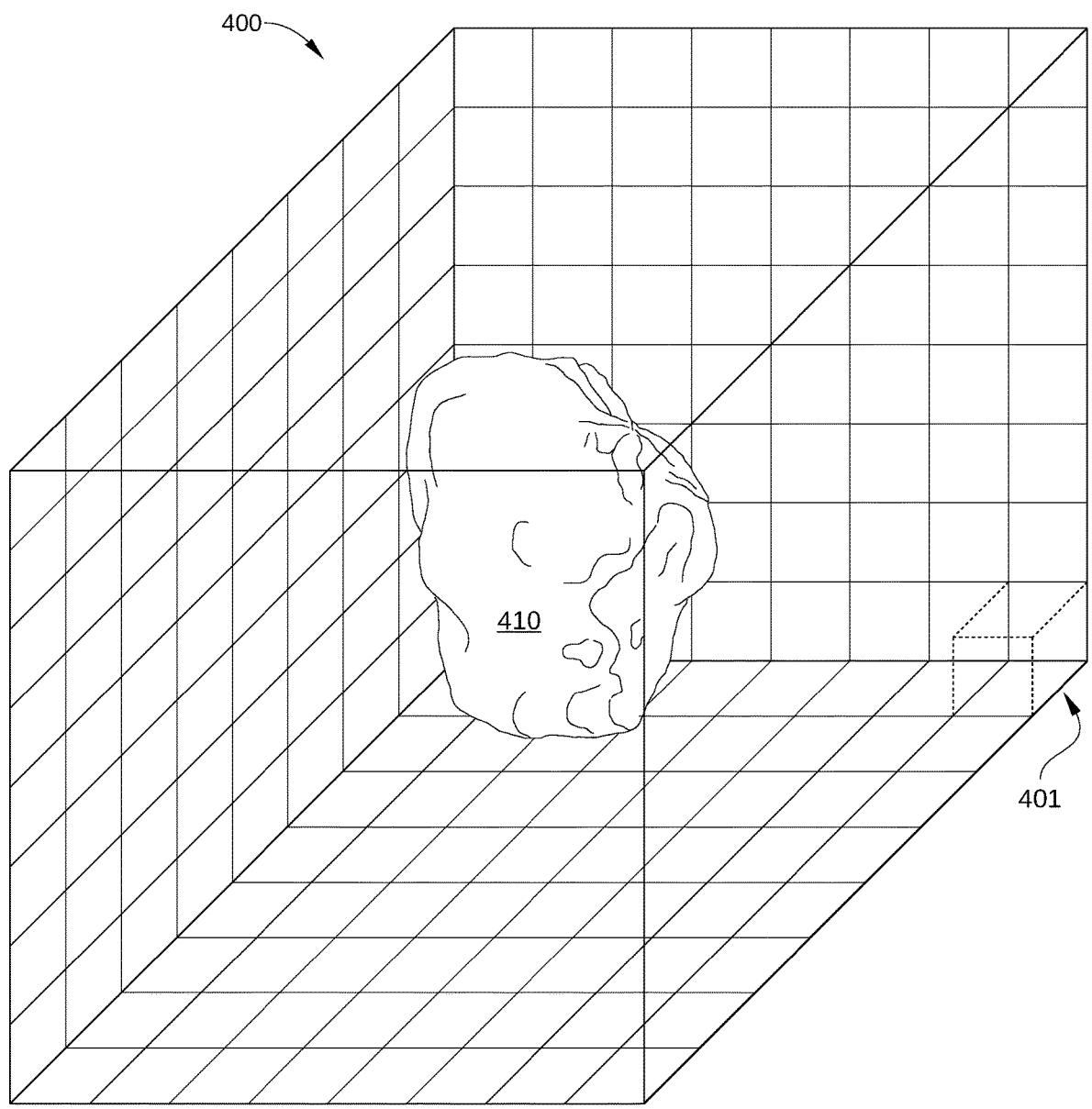
FIG. 4 schematically illustrates a digital volume that is constructed based on projection images generated by one or more X-ray images included in the radiation therapy system of FIG. 1, according to various embodiments.

FIG. 4 schematically illustrates a digital volume 400 that is constructed based on projection images generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for subclinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, in some embodiments, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway.

Generation of Scatter-Estimate Kernels

According to various embodiments, 2D projection images acquired by RT system 100 or some other imaging system are corrected using model-based physics kernels. More specifically, a scatter component that is included in a 2D projection image and is caused by a specific hardware-related scatter source is removed via a set of scatter-estimate kernels that estimate the scatter component. The set of scatter-estimate kernels is convolved with the 2D projection image to estimate the scatter component, and a corrected 2D projection image is generated by subtracting the estimated scatter component. Thus, the contribution of a specific hardware-related scatter source can be removed from an acquired 2D projection image. According to various embodiments, the scatter-estimate kernels are generated prior to the acquisition of 2D projection images from which a scatter component is to be removed. The generation of scatter-estimate kernels suitable for determining a scatter component caused by hardware-related scatter sources is described below in conjunction with FIGS. 5-7.

Figure 5:
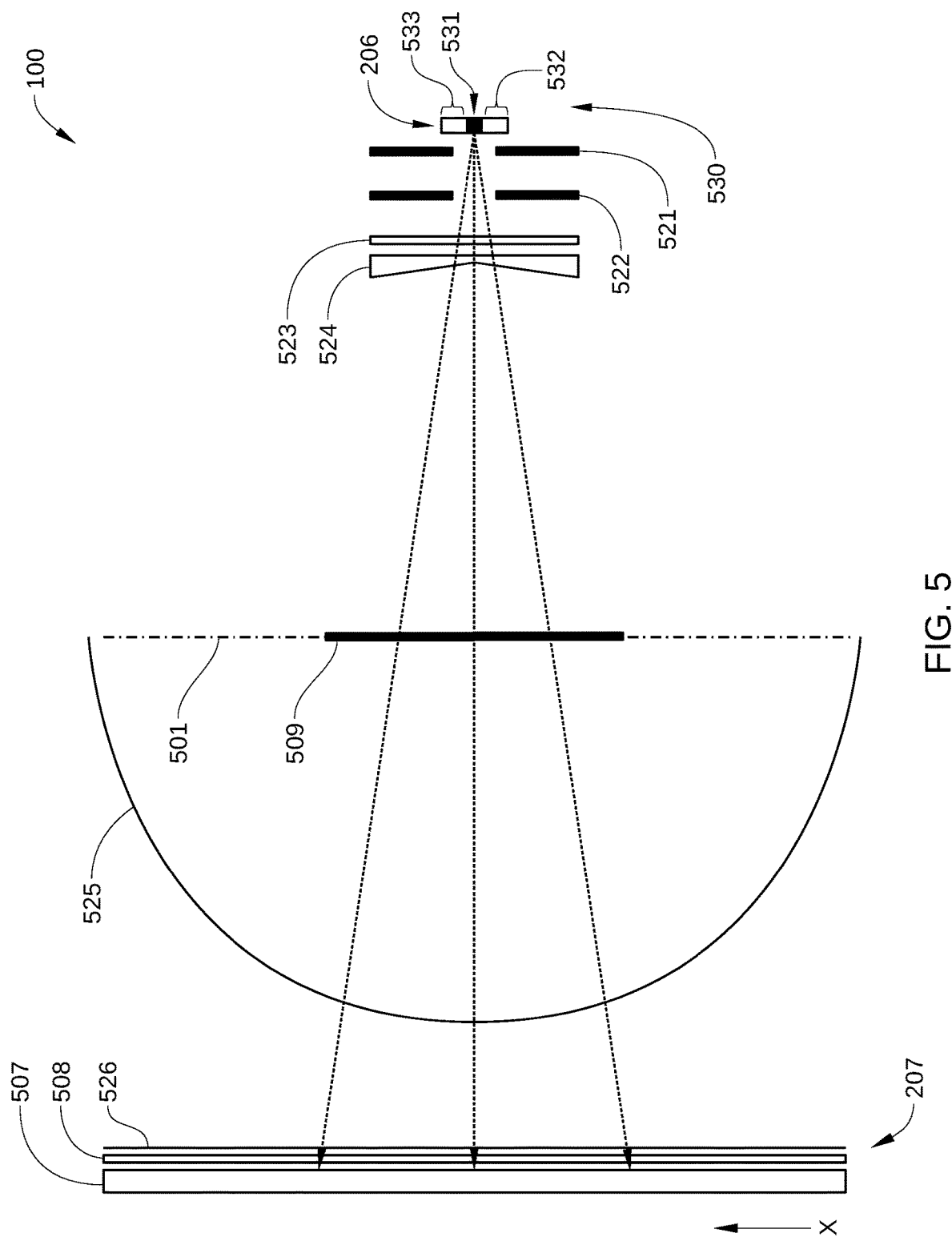
FIG. 5 schematically illustrates elements of the radiation therapy system of FIG. 1 that are associated with scatter components that can be included in projection images acquired by the radiation therapy system of FIG. 1, according to various embodiments.

FIG. 5 schematically illustrates elements of RT system 100 that are associated with scatter components that can be included in projection images acquired by RT system 100, according to various embodiments. FIG. 5 further illustrates various factors that affect the generation of the scatter-estimate kernels for determining scatter components caused by hardware-related scatter sources within RT system 100. As shown, an object 509 is disposed between imaging X-ray source 206 and X-ray imager 207 and is positioned on an isoplane 501 that passes through an isocenter of RT system 100. X-ray imager 207 includes a detector array 507, an anti-scatter grid 508, and a detector cover 526, while X-ray source 206 includes a beam spot 530 for generating an imaging beam (such as imaging X-rays 231 in FIG. 2). Also shown are a diaphragm 521, X-blades 522 of a collimator, Y-blades (not shown) of the collimator, a filter 523, a bow-tie filter 524, and, in some embodiments, a bore 525. Beam spot 530 includes a primary focus 531, which generates most of the imaging beam, and off-focal regions 532 and 533, which are located outside primary focus 531 and generate a smaller portion of the imaging beam.

Sources of X-ray scatter in RT system 100 can include filter 523, bow-tie filter 524, bore 525, detector cover 526 of X-ray imager 207, and/or other components of X-ray imager 207. In some embodiments, X-ray source 206 can include additional elements (not shown) that can contribute to inherent filtration and therefore cause X-ray scatter, such as a tube glass, an insert window, dielectric oil, and/or a front window of X-ray source 206. Further, in some embodiments, off-focal regions 532 and 533 generate portions of the imaging beam that can cause blurring and/or loss of contrast in a projection image acquired by X-ray imager 207. Such blurring and loss of contrast is similar to effects caused by other scatter sources. In such embodiments, off-focal regions 532 and 533 can be treated as a hardware-related scatter source within RT system 100.

According to various embodiments, scatter-estimate kernels are generated for some or all of the above-described hardware-related scatter sources within RT system 100. A set of one or more such scatter-estimate kernels enables the determination of a scatter component that is associated with a particular hardware-related scatter source and therefore is included in 2D projection images acquired by RT system 100. More specifically, convolution of a suitable set of scatter-estimate kernels with an acquired 2D projection image produces an estimated scatter component associated with that particular hardware-related scatter source. In the embodiments, a corrected projection image can then be generated by subtraction of the estimated scatter component from the acquired 2D projection image.

According to various embodiments, the scatter-estimate kernels for hardware-related scatter sources within RT system 100 are model-based physics kernels that are generated via simulations that accurately model the behavior of X-rays within RT system 100. In such embodiments, most or all hardware elements included in the image acquisition chain of RT system 100 may be included, so that a scatter component associated with a particular hardware-related scatter source can be accurately determined for all portions of a projection image. Examples of hardware elements included in the image acquisition chain of RT system 100 include beam spot 530, diaphragm 521, X-blades 522 of the collimator, Y-blades of the collimator, filter 523, bow-tie filter 524, bore 525, components of X-ray imager 207 (such as anti-scatter grid 508 and the various layers of detector array 507), and components of X-ray source 206 that can contribute to inherent filtration (such as a tube glass, an insert window, dielectric oil, and/or a front window of X-ray source 206). The various layers (not shown for clarity) of detector array 507 can include a scintillator layer and a tungsten backscatter layer.

In some embodiments, each scatter-estimate kernel is generated via Monte Carlo simulations that accurately model the physics of X-ray behavior within the image acquisition chain. For example, in some embodiments, Monte Carlo inputs (e.g., photon phase space, model of the energy deposition in the detector, angular and energy dependence of a given scatter, and the like) and specific ray-tracing can be combined analytically to generate the kernels. In some embodiments, the accuracy of the physics modeling is improved by including precise dimensions, composition, and relative positions of various components of X-ray source 206, such as the X-ray tube anode and front window, beam spot 530, diaphragm 521, X-blades 522 and Y-blades of the collimator, filter 523, and bow-tie filter 524. Such information enables an accurate beam profile to be determined for an imaging beam of a known energy. Similarly, in such embodiments, the accuracy of the physics modeling is improved by including precise dimensions and relative positions of various components of X-ray imager 207, such as the precise composition of each layer of detector array 507 and anti-scatter grid 508 and the scatter transmission of anti-scatter grid 508. Such information provides the angular-dependent response of X-ray imager 207.

In some embodiments, a set of scatter-estimate kernels for a particular hardware-related scatter source is implemented as a single 2D kernel for convolution with 2D projection images. In such embodiments, the single 2D kernel can provide an accurate estimate of a scatter component caused by a particular hardware-related scatter source when the attenuated beam that strikes that particular scatter source is known. For example, in some instances, a single 2D kernel can provide an accurate estimate of a scatter component caused by scatter sources located between object 509 and detector array 507, such as bore 525 or anti-scatter grid 508. In such embodiments, pencil-beam and monoenergetic simulations can be performed using a detailed model of the geometry and composition of the various layers of detector array 507 to obtain energy-dependent scatter-estimate kernels for X-ray imager 207, bore 525, or some other hardware-related scatter source disposed between object 509 and detector array 507. Generally, such a scatter-estimate kernel is based on multiple factors, such as imaging beam energy, a distance 502 between isoplane 501 and X-ray imager 207, the configuration of detector array 507, the configuration of anti-scatter grid 508, and/or the like. Consequently, for a particular hardware-related scatter source, a plurality of 2D scatter-estimate kernels can be generated, where each 2D scatter-estimate kernel is generated for a different combination of such factors.

In some embodiments, a set of scatter-estimate kernels for a particular hardware-related scatter source is implemented as a plurality of sub-kernels for convolution with 2D projection images. In such embodiments, each sub-kernel is for convolution with a different portion of a 2D projection image, such as a single column of pixels or a group of multiple contiguous columns of pixels. Consequently, in such embodiments, for a particular hardware-related scatter source, position dependence (in the plane of a detector array of X-ray imager 207) of the scatter-estimate kernels can be incorporated into the sub-kernels that are selected to form a set. For example, in such embodiments, each sub-kernel is for convolution with a different portion of a 2D projection image, and each different portion of the 2D projection image corresponds to a different position or region in a detector array plane of X-ray imager 207. Thus, when scatter caused by a particular hardware-related scatter source has a strong dependence along one dimension of X-ray imager 207 (for example along an X-direction), a different sub-kernel can be selected for different positions of X-ray imager 207 along that dimension. One such embodiment is described below in conjunction with FIG. 6.

Figure 6:
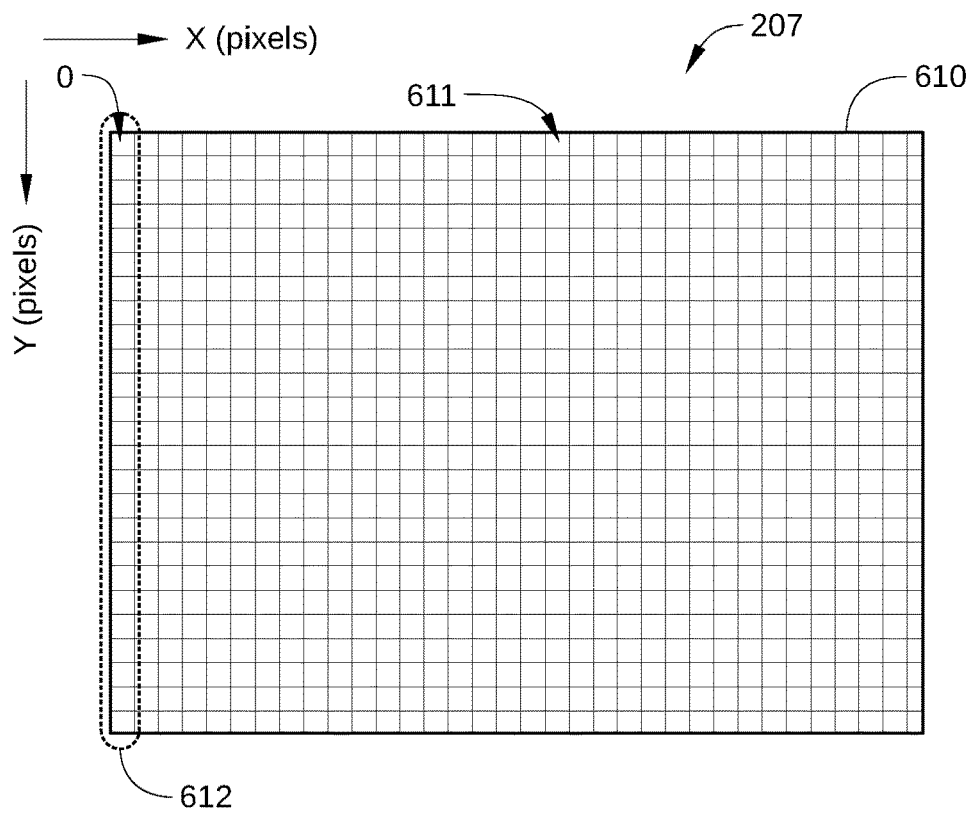
FIG. 6 schematically illustrates a detector array of an X-ray imager and a 2D projection image acquired by the X-ray imager, according to various embodiments.
Figure 6:
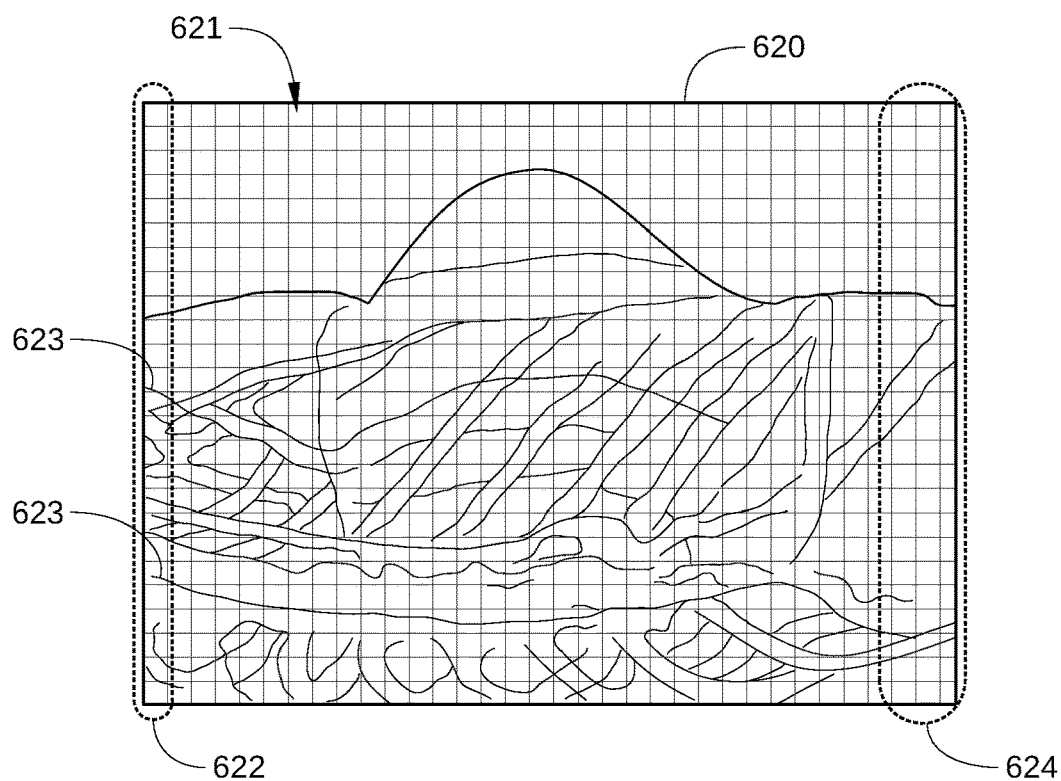

FIG. 6 schematically illustrates a detector array 610 of X-ray imager 207 and a 2D projection image 620 acquired by X-ray imager 207, according to various embodiments. In some embodiments, detector array 610 includes a surface with a matrix or array of pixel detector elements 611 formed thereon. In the embodiment illustrated in FIG. 6, pixel detector elements 611 are arranged in a rectangular pixel coordinate system of rows and columns having an origin 0 located at a corner of detector array 610. Further, in the embodiment illustrated in FIG. 6, detector array 610 is configured as a 25×34 pixel array, but in practice detector array 610 is typically hundreds or thousands of pixels in height and width. Each pixel detector element 611 generates a signal (e.g., a voltage that is proportional to incident X-ray intensity) for a different pixel 621 of what will eventually become a digital image, such as 2D projection image 620. Generally, each pixel 621 of 2D projection image 620 has a gray level associated therewith that is proportional to such a signal. These varying gray levels are depicted schematically in FIG. 6 as contour lines 623 that visualize patient anatomy. For clarity, contour lines 623 and the associated visualized patient anatomy have exaggerated resolution in FIG. 6. In practice, such contour lines and visualized patient anatomy have a resolution that is defined by the resolution of pixels 621. In some embodiments, X-ray imager 207 includes a scintillator layer that emits light when excited by incident X-rays, and each pixel detector element 611 includes a photodiode that detects the emitted light and generates a signal for a corresponding pixel 621 of a 2D projection image 620.

As noted above, a set of scatter-estimate kernels for a particular hardware-related scatter source can include a plurality of sub-kernels for convolution with a 2D projection image, such as 2D projection image 620. In such embodiments, each sub-kernel is for convolution with a different portion of 2D projection image 620, and each different portion of 2D projection image 620 is associated with a different position or region in detector array 610. In some embodiments, the position or region in detector array 610 corresponds to a single column 612 of pixel detector elements that spans detector array 610 in one direction, for example in a Y-direction in FIG. 6. For example, in the embodiment illustrated in FIG. 6, the single column 612 of pixel detector elements 611 corresponds to a single column 622 of pixels 621 in 2D projection image 620, and a sub-kernel in the set of scatter estimate kernels is for convolution with single column 622 of pixels 621. Thus, in the embodiment, a different sub-kernel in the set of scatter estimate kernels is for convolution with a different column of pixels 621 of 2D projection image 620. Alternatively, in some embodiments, the position or region in detector array 610 corresponds to a group of multiple contiguous columns 624 of pixels 621 in 2D projection image 620. In such embodiments, one sub-kernel in the set of scatter-estimate kernels is for convolution with the group of multiple contiguous columns 624 of pixels 621, and other sub-kernels are for convolution with other groups of multiple contiguous columns of pixels 621. As shown, each group of multiple contiguous columns 624 spans detector array 610 in one direction, for example in a Y-direction in FIG. 6.

In some embodiments, sets of contiguous columns 624 of pixels are binned to reduce the number of sub-kernels to be computed for a particular hardware-related scatter source. For example, in one such embodiment, in which 2D projection image includes 200 columns of pixels 621, columns 0-19 are associated with a first bin, columns 20-39 are associated with a second bin, columns 30-49 are associated with a third bin, and so on. In such embodiments, the same sub-kernel in the set of scatter estimate kernels is for use with each column within a particular bin of columns. Thus, a first sub-kernel is for use with the columns of the first bin, a second sub-kernel is for use with the columns of the second bin, a third sub-kernel is for use with the columns of the third bin, and so on.

In some embodiments, a set of scatter-estimate kernels includes a plurality of sub-kernels (as described above in conjunction with FIG. 6) when the effects of a particular hardware-related scatter source span a small number of pixels in a direction perpendicular to the columns of pixels. Thus, in FIG. 6, when the effects of a particular hardware-related scatter source span a small number of pixels in an X-direction, each sub-kernel is for convolution with a single column (or small number of columns) of pixels in 2D projection image 620 that span a Y-direction of 2D projection image 620. One such embodiment is described below in conjunction with FIG. 7.

Figure 7:
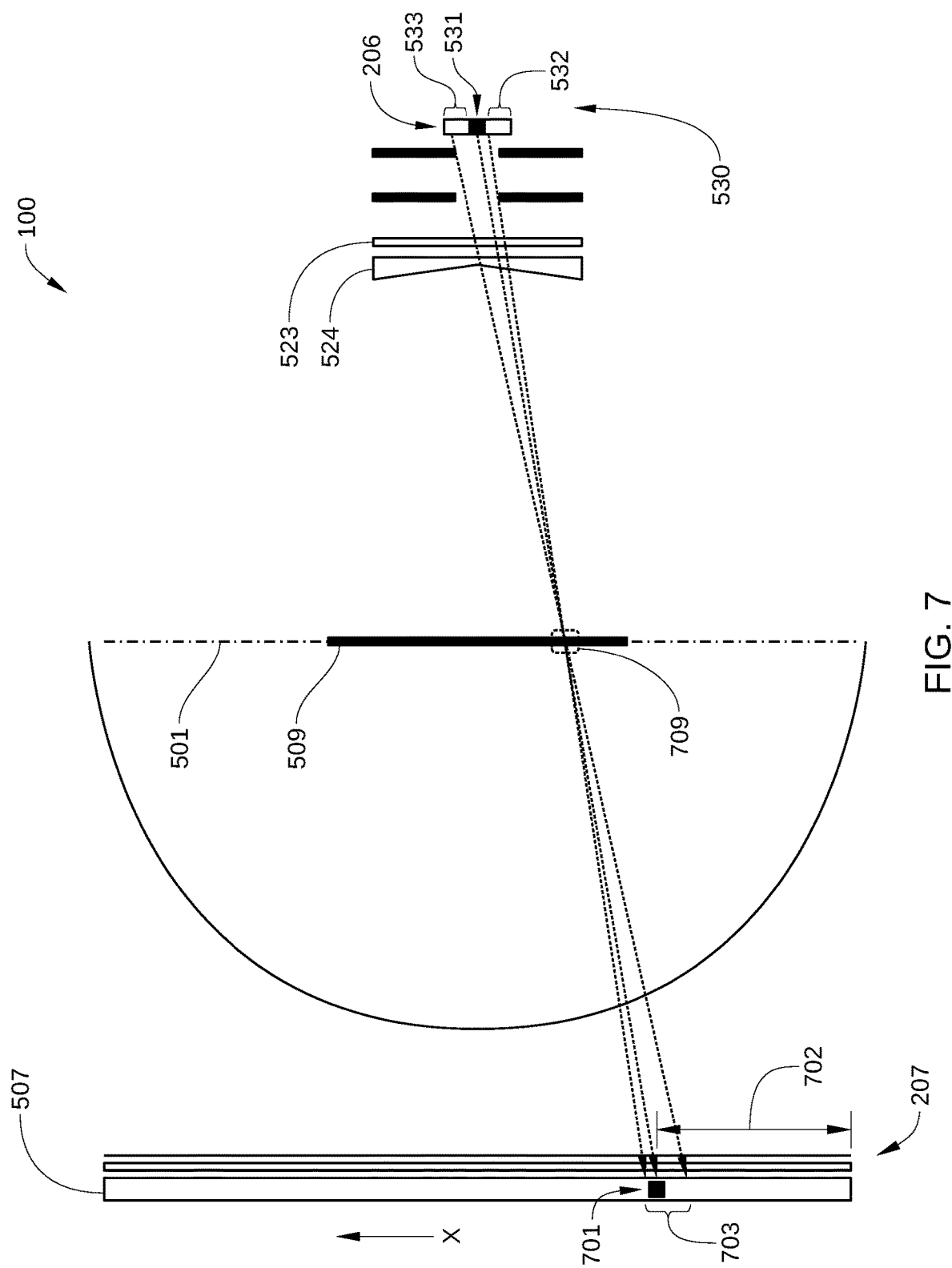
FIG. 7 schematically illustrates elements of the radiation therapy system of FIG. 1 that are associated with off-focal radiation and factors associated with generating a scatter-estimate kernel for off-focal radiation, according to various embodiments.

FIG. 7 schematically illustrates elements of RT system 100 that are associated with off-focal radiation and factors associated with generating a scatter-estimate kernel for off-focal radiation, according to various embodiments. The configuration of RT system 100 depicted in FIG. 7 is substantially similar to that depicted in FIG. 5. In addition, FIG. 7 shows a particular pixel detector element 701 in detector array 507 that is disposed at an X-position 702 in X-ray imager 207. Pixel detector element 701 is included in a column of pixel detector elements that spans detector array 507 in a Y-direction (into page).

In some embodiments, the column of pixel detector elements that includes pixel detector element 701 (referred to herein as the "column of interest") corresponds to a sub-kernel in a set of scatter-estimate kernels. In such embodiments, the set of scatter-estimate kernels is for determining a scatter component caused by off-focal radiation in a 2D projection image acquired by X-ray imager 207, and includes a plurality of sub-kernels. Off-focal radiation is caused within an X-ray source by electrons that impinge the anode of a kV tube in X-ray source 206 and then bounce back. Reaccelerated in the electric field of the X-ray source, these electrons can produce photons away from the primary focus when they again collide with the anode. As a result, this so-called "off-focal" radiation creates an extended secondary source, depicted by off-focal regions 532 and 533, that is located outside primary focus 531 of beam spot 530.

According to various embodiments, a sub-kernel is analytically computed for a particular column of interest (or bin of columns of interest), where each column of interest has a different X-position in detector array 507. In some embodiments, each column of interest of detector array 507 corresponds to a single column of pixel detector elements, and in other embodiments, each column of interest of detector array 507 corresponds to multiple contiguous columns of pixel detector elements of detector array 507. In either case, a sub-kernel for each column of interest can be computed to determine a scatter component caused by off-focal radiation in a 2D projection image. This is because the blurring and loss of contrast caused by the off-focal radiation from off-focal regions 532 and 533 spans a small number of pixels in the X-direction, as shown in FIG. 7. Specifically, for pixel detector element 701, the effect of off-focal radiation from off-focal regions 532 and 533 spans a narrow region 703 around pixel detector element 701.

In some embodiments, a plurality of sub-kernels is analytically computed for a particular column of interest, where each sub-kernel is analytically computed based on many different imaging conditions. Therefore, in such embodiments, the scatter component that is associated with that particular column of interest can be determined for each of the many different imaging conditions. Thus, for a particular column of interest, a different sub-kernel for determining such a scatter component is analytically computed based on various combinations of different factors. Such factors can include a beam energy for the imaging beam generated by beam spot 530, a gantry projection angle associated with a 2D projection image that is to be convolved with the sub-kernel, an assumed off-focal radiation intensity in off-focal regions 532 and 533, an intensity distribution in off-focal regions 532 and 533, an attenuation caused by bow-tie filter 524 and/or filter 523, and/or an attenuation caused by object 509.

In some embodiments, for a particular column of interest, a sub-kernel for determining a scatter component that is caused by off-focal radiation is computed based on attenuation of the off-focal radiation by object 509. In such embodiments, when analytically computing the sub-kernel, such attenuation of off-focal radiation can be determined based on a path length through object 509. In such embodiments, a 3D model or approximated 3D model of object 509 can be employed to determine the path length, and from the path length and material composition of object 509, a transmission indicator can be determined. Thus, for a particular column of interest, for each gantry projection angle, a different transmission indicator for object 509 can be determined. Alternatively, in some embodiments, when analytically computing the sub-kernel, attenuation of off-focal radiation by object 509 can be determined based on a portion 709 of object 509 through which rays pass when traced from beam spot 530 to the column of interest. In such embodiments, object 509 is collapsed to a 2D object, in which the mass of object 209 is concentrated in a plane (shown edge-on in FIG. 7) located between X-ray source 206 and X-ray imager 207. In the embodiment illustrated in FIG. 7, such a plane is disposed at isoplane 501 of RT system 100, while in other embodiments, such a plane can be disposed at any other suitable location between X-ray source 206 and X-ray imager 207. Because the attenuating properties of object 509 typically vary along the length of object 509, a transmission indicator for each column of interest can be determined based on the location of portion 709 along the length of object 509.

In some embodiments, the transmission indicator can be single value, such as a percentage of transmission of incident X-rays through object 509. Alternatively, in some embodiments, the transmission indicator can be an indicator of beam hardening, in which X-rays of lower energies wavelengths are more attenuated than X-rays of higher energies when such X-ray pass through object 509. In such embodiments, the transmission indicator can be a function of the transmission of various photon wavelengths. In either case, selection of sub-kernels for a particular column of interest based in part on a transmission indicator enables the computed sub-kernels to consider the energy dependence of certain hardware-related scatter sources, such as bow-tie filter 524.

In some embodiments, for a particular column of interest, a sub-kernel for determining a scatter component that is caused by off-focal radiation is further based on attenuation of the off-focal radiation by filter 523 and/or bow-tie filter 524. In some embodiments, for a particular column of interest, a transmission indicator for filter 523 and/or bow-tie filter 524 may be based on path length within filter 523 and/or bow-tie filter 524. Thus, for a particular column of interest, a plurality of sub-kernels is computed based on different combinations of various levels of attenuation of the off-focal radiation by filter 523 and/or bow-tie filter 524. Levels of attenuation by filter 523 and/or bow-tie filter 524 can be a transmission indicator, such as a transmission value or a function of the transmission of various photon energies.

As noted previously, in some embodiments, when the effects of a particular hardware-related scatter source span a small number of pixels in a direction perpendicular to the columns of pixels, a set of scatter-estimate kernels for the particular hardware-related scatter source can include a plurality of sub-kernels that are each for convolution with a single column (or small number of columns) of pixels of a 2D projection image. In the embodiment illustrated in FIG. 7, the hardware-related scatter source is off-focal radiation associated with off-focal regions 532 and 533. In other embodiments, a set of scatter-estimate kernels for other hardware-related scatter sources can be generated in a similar fashion. For example, in some embodiments, a set of scatter-estimate kernels for bow-tie filter 524 can include a plurality of sub-kernels, where each sub-kernel is for convolution with a single column (or small number of columns) of pixels of a 2D projection image. Scatter caused by bow-tie filter 524 varies strongly along one dimension of detector array 507 (for example along the X-direction in the embodiment illustrated in FIGS. 5 and 7). Consequently, a set of scatter-estimate kernels that includes a plurality of sub-kernels for different X-positions of detector array 507 can accurately determine a scatter component caused by bow-tie filter 524. Similar to the sub-kernels computed to determine a scatter component caused by off-focal radiation, the sub-kernels selected for determining a scatter component caused by bow-tie filter 524 are also computed based on additional factors, such as imaging beam energy and attenuation caused by object 509.

Scatter Correction of X-Ray Projection Images

Figure 8:
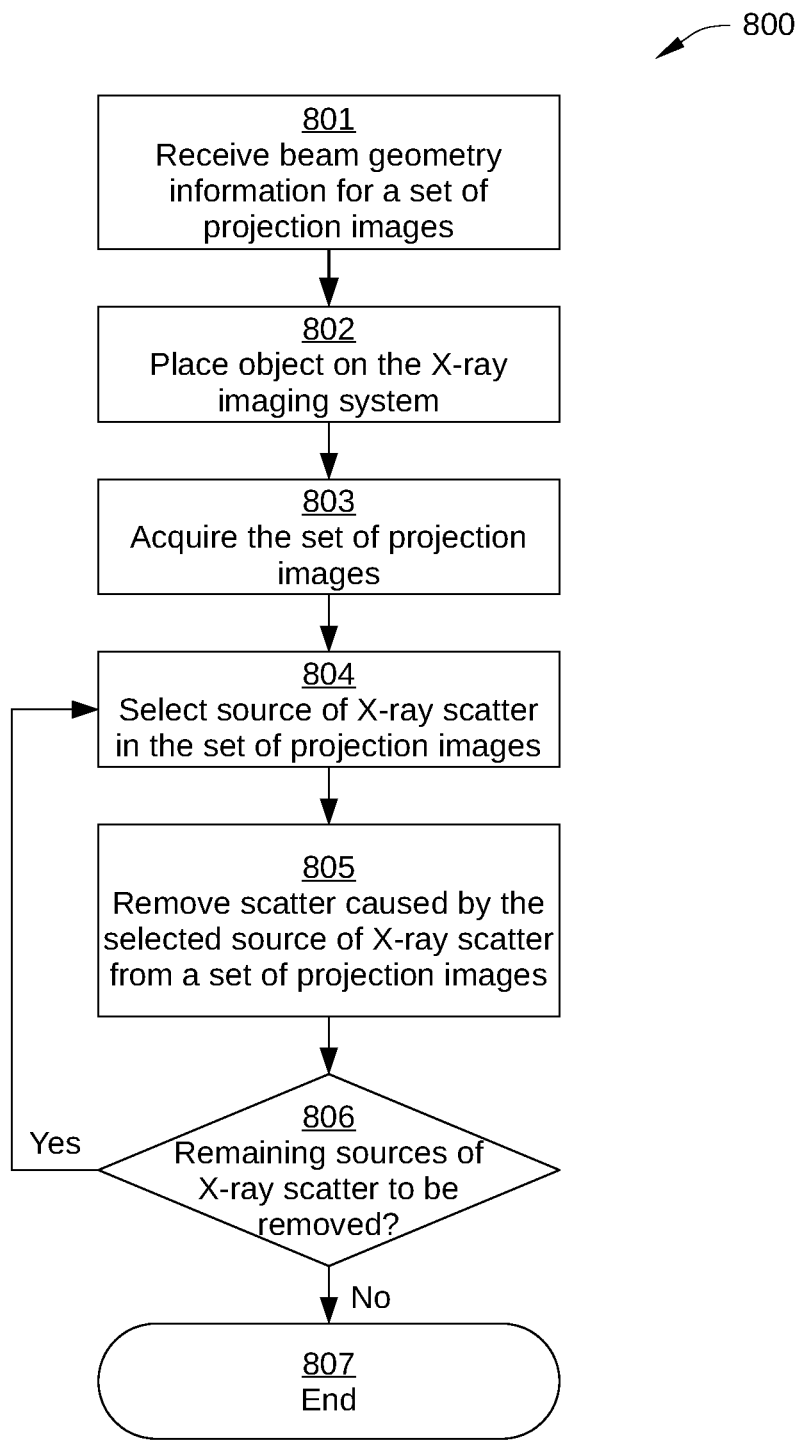
FIG. 8 sets forth a flowchart of a process for generating a set of corrected 2D projection images, according to one or more embodiments.

FIG. 8 sets forth a flowchart of a process 800 for generating a set of corrected 2D projection images, according to one or more embodiments. Process 800 can be implemented as part of an imaging-only process, or in conjunction with radiation therapy, such as IGRT, stereotactic radiosurgery (SRS), and the like. Process 800 may include one or more operations, functions, or actions as illustrated by one or more of blocks 801-807. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although process 800 is described in conjunction with the X-ray imaging system described herein as part of RT system 100 and FIGS. 1-7, persons skilled in the art will understand that performance of process 800 by any suitably configured X-ray imaging system is within the scope of the present embodiments.

In step 801, the X-ray imaging system of RT system 100 receives beam geometry information for a set of 2D projection images that are to be acquired. For example, in some embodiments, the set of 2D projection images are used to reconstruct a digital volume, such as digital volume 400 in FIG. 4.

In step 802, an object or patient is placed on or within the X-ray imaging system of RT system 100, such as on couch 107. For example, in some embodiments, a patient is positioned on couch 107 so that a region of interest of patient anatomy is disposed proximate isocenter 203 of RT system 100. Alternatively, an object is positioned so that a region of interest of the object is disposed proximate an isocenter of an imaging system.

In step 803, a set of 2D projection images of the region of interest are acquired. In some embodiments, the set of 2D projection images are acquired via a CBCT acquisition process. Thus, in such embodiments, the set of 2D projection images can include hundreds to thousands of projection images that are each acquired at a different gantry projection angle.

In step 804, a particular source of X-ray scatter is selected that is associated with the X-ray imaging system that acquired the set of 2D projection images in step 803. Generally, the selected source of X-ray scatter is associated with a specific hardware component or element of the X-ray imaging system that acquired the set of 2D projection images. Thus, the selected source of X-ray scatter does not include the object or region of patient anatomy being imaged. For example, for the X-ray imaging system of RT system 100, the possible sources of X-ray scatter that can be selected in step 804 may be associated with an X-ray filter of RT system 100 (such as a bow-tie filter or a uniform filter), a bore of the imaging system, off-focal radiation generated by a beam spot of the imaging system, or one or more components of an X-ray detector of the imaging system, among others. It is noted that each such hardware component or element of the X-ray imaging system can contribute a different scatter component to the projection images in the set of 2D projection images.

In some embodiments, the particular source of X-ray scatter that is selected in the first iteration of step 804 is the source of X-ray scatter that contributes the largest scatter component to the projection images in the set of 2D projection images. The source of X-ray scatter that contributes the largest scatter component can vary depending on the configuration of the imaging system that generates the 2D projection images. In some instances, such a source of X-ray scatter can be a bow-tie filter of the imaging system or off-focal radiation proximate a beam spot of the imaging system. In such embodiments, because the largest source of noise associated with X-ray scatter is removed in the first iteration of steps 804-806, more accurate estimates of the scatter components for other sources of X-ray scatter can be computed in subsequent iterations of steps 804-806. As described in greater detail below, this is because a scatter component in a 2D projection image is determined by convolving a set of scatter-estimate kernels with the image, and such scatter-estimate kernels are computed to be convolved with a scatter-free projection image. Therefore, a scatter component determined in this way inherently includes a level of inaccuracy roughly proportional to the magnitude of the scatter component that exists in the 2D projection image at the time of convolution.

In step 805, a scatter component caused by the selected source of X-ray scatter is removed from a set of 2D projection images that are based on the 2D projection images acquired in step 803. Thus, in step 805, a set of corrected projection images is generated by the removal of the scatter component caused by the selected source of X-ray scatter. In a first iteration of steps 804-806, the set of 2D projection images is the set of 2D projection images acquired in step 803. In subsequent iterations of steps 804-806, the set of 2D projection images can be the set of corrected projection images from a preceding iteration of steps 804-806. Various embodiments for the removal of a scatter component associated with a particular source of X-ray scatter are described below in conjunction with FIG. 9.

In step 806, the X-ray imaging system determines whether there are any remaining sources of X-ray scatter to be removed from the set of corrected projection images. If yes, method 800 returns to step 804; if no, method 800 proceeds to step 807 and terminates.

In the embodiment described above in conjunction with FIG. 8, a scatter component associated with a selected source of X-ray scatter can be removed from a set of 2D projection images over multiple iteration of steps 804-806. This process is then repeated for one or more additional scatter components. In other embodiments, an alternative iteration scheme is employed, in which a global loop is performed. In such embodiments, in one iteration of the global loop, one iteration of steps 804-806 is performed for each scatter component to be removed. One or more additional iterations of the global loop are then performed to further refine the set of 2D projection images. In some embodiments, in later iteration of the global loop, an iteration of steps 804-806 is performed for each scatter component to be removed. In other embodiments, in later iterations of the global loop, an iteration of steps 804-806 is performed for selected scatter components to be removed, such as scatter components that are assumed to effect a larger contribution to the set of 2D projection images.

Figure 9:
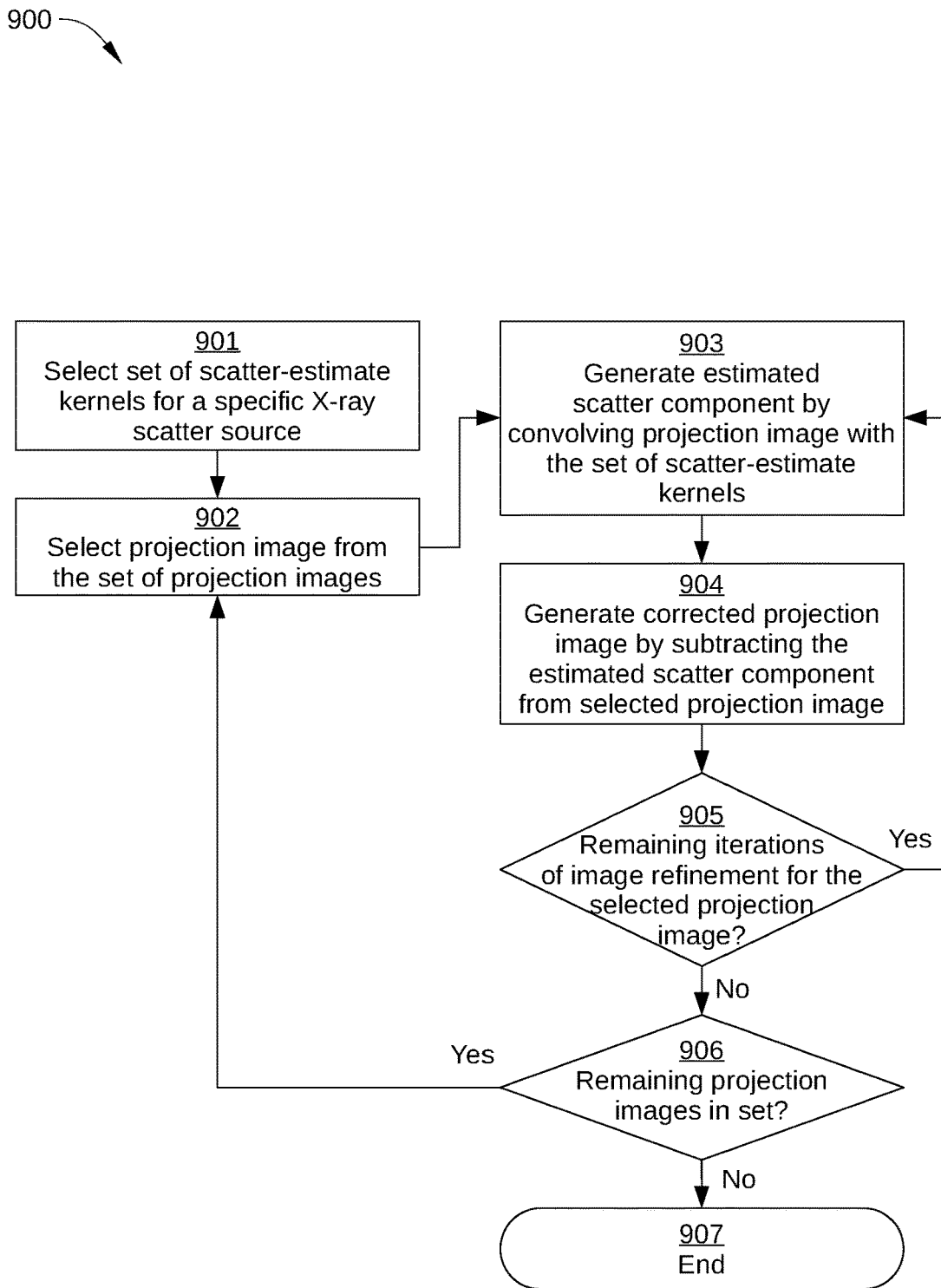
FIG. 9 sets forth a flowchart of a computer-implemented process 900 for removing a scatter component from a set of one or multiple X-ray projection images, according to various embodiments.

FIG. 9 sets forth a flowchart of a computer-implemented process 900 for removing a scatter component from a set of one or multiple X-ray projection images, according to various embodiments. More specifically, the scatter component that process 900 removes from the set of X-ray projection images is caused by a specific source of X-ray scatter within the imaging system that acquired the set of projection images. As noted previously, examples of such sources of X-ray scatter include an X-ray filter of RT system 100 (such as a bow-tie filter or a plate filter), a bore of RT system 100, off-focal radiation generated by a beam spot of RT system 100, or one or more components of an X-ray detector of RT system 100, and the like. In some embodiments, process 900 can be implemented as part of a process for generating a set of corrected 2D projection images, such as process 800 in FIG. 8. In such embodiments, process 900 can be implemented as an embodiment of step 805 in process 800, and the set of multiple X-ray projection images referenced in process 900 corresponds to the set of 2D projection images of a region of interest acquired by RT system 100 in step 803 of process 800.

Process 900 may include one or more operations, functions, or actions as illustrated by one or more of blocks 901-907. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although process 900 is described in conjunction with the X-ray imaging system described herein as part of RT system 100 and FIGS. 1-8, persons skilled in the art will understand that performance of process 900 by any suitably configured X-ray imaging system is within the scope of the present embodiments.

In step 901, the X-ray imaging system of RT system 100 selects or retrieves a set of scatter-estimate kernels for a specific X-ray scatter source, such as the source of X-ray scatter selected in step 804 of process 800. The set of scatter-estimate kernels is constructed so that, when a projection image is convolved with the set of scatter-estimate kernels, an estimated scatter component is generated that indicates a contribution to the projection image caused by the specific X-ray scatter source. Thus, subtraction of the estimated scatter component from the projection image produces a corrected projection image that has been refined by the removal of at least a portion of the X-ray scatter introduced by the specific X-ray scatter source.

In some embodiments, the set of scatter-estimate kernels are retrieved from a database associated with RT system 100, such as a database stored in or accessible by image acquisition and treatment control computer 106 and/or remote control console 110. For some hardware-related scatter sources, the set of scatter-estimate kernels retrieved from the database includes a 2D kernel that is for convolution with a complete 2D projection image. For example, such hardware-related scatter sources include scatter sources disposed between imaging X-ray source 206 and X-ray imager 207, such as bore 525, detector cover 526, internal detector scatter, and the like. For other hardware-related scatter sources, the set of scatter-estimate kernels retrieved from the database includes a plurality of sub-kernels that are each for convolution with a different portion of a particular 2D projection image. For example, in some embodiments, such hardware-related scatter sources include scatter sources that are disposed on a source-side of object 509, such as filter 523, bow-tie filter 524, off-focal regions 532 and 533, and the like.

In some embodiments, a single set of scatter-estimate kernels is retrieved in step 901 for convolution with the projection images in the set of 2D projection images to be corrected. In such embodiments, the same set of scatter-estimate kernels is convolved with all projection images in the set of 2D projection images to be corrected. For example, in some embodiments, the same set of scatter-estimate kernels is convolved with all projection images in the set of 2D projection images when scatter caused by the hardware-related scatter source is not dependent on the X-position 702 of a pixel detector element 701 in X-ray imager 207. Generally, scatter caused by a hardware-related scatter source is not dependent on attenuation by object 509 or on X-position 702 of a pixel detector element 701 when the hardware-related scatter source is disposed between imaging X-ray source 206 and X-ray imager 207.

In some embodiments, a different set of scatter-estimate kernels is retrieved in step 901 for convolution with each projection image in the set of 2D projection images to be corrected. In such embodiments, a different set of scatter-estimate kernels is convolved with each different projection image in the set of 2D projection images to be corrected. For example, in some embodiments, a different set of scatter-estimate kernels is convolved with each different projection image in the set of 2D projection images when scatter caused by the hardware-related scatter source is dependent on attenuation by object 509. Generally, scatter caused by a hardware-related scatter source is dependent on attenuation by object 509 when the hardware-related scatter source is disposed on a source-side of imaging X-ray source 206. This is because attenuation of an imaging beam by object 509 varies with gantry projection angle, and therefore the imaging beam for each projection image in the set of 2D projection images to be corrected has undergone different attenuation by object 509. Consequently, a different set of scatter-estimate kernels is computed for each such attenuation by object 509.

In some embodiments, in step 901 selection of the set or sets of scatter-estimate kernels for a specific X-ray scatter source is based on multiple factors. In some embodiments, such factors include the imaging beam energy associated with acquisition of the set of 2D projection images, the X-position 702 of a pixel detector element 701 (or group of contiguous pixel detector elements) in X-ray imager 207, and/or a transmission indicator that quantifies attenuation of the imaging beam by object 509. For example, in one such embodiment, for a particular column of pixel detector elements 701 that correspond to a column of a 2D projection image to be corrected, a sub-kernel is selected based on the imaging beam energy employed to acquire the 2D projection image, the X-position 702 of the particular column, and a transmission indicator that is associated with a specific attenuation of the imaging beam by object 509 for the 2D projection image and at the X-position of particular column. In the embodiment, a different sub-kernel is selected for each column or group of columns of pixel detector elements 701. Further, in the embodiment, the retrieved sub-kernels are computed to account for other factors associated with the configuration of RT system 100 that was employed to acquire the set of 2D projection images, such as the size, shape, and location of X-ray filters that the imaging beam passes through (e.g., filter 523 and/or bow-tie filter 524); the configuration of anti-scatter grid 508 and/or other layers included in X-ray imager 207, inherent filtration of the imaging beam by components of imaging X-ray source 206; and the like.

In step 902, the X-ray imaging system of RT system 100 selects a 2D projection image from the set of projection images to be corrected.

In step 903, the X-ray imaging system of RT system 100 generates an estimated scatter component for the hardware-related scatter source. In some embodiments, an estimated scatter component for a 2D projection image includes a value for each pixel included in the 2D projection image, where the value represents a magnitude of X-ray scatter signal determined to be caused by the hardware-related scatter source at the location of the pixel.

To generate the estimated scatter component, the X-ray imaging system of RT system 100 convolves the selected 2D projection image with the set of scatter-estimate kernels selected in step 902 for the selected 2D projection image. In some embodiments, a single 2D kernel is convolved with the selected 2D projection image in order to generate the estimated scatter component for the hardware-related scatter source. In other embodiments, a set of multiple sub-kernels is convolved with the selected 2D projection image. In such embodiments, each sub-kernel is convolved with a different portion of the 2D projection image via a one-dimensional convolution. For example, in some embodiments, each sub-kernel in the set of scatter-estimate kernels is convolved with a different column of pixels of the 2D projection image. Taken together, the output from the convolution of each sub-kernel forms a complete estimated scatter component for the selected 2D projection image.

In step 904, the X-ray imaging system of RT system 100 generates a corrected projection image. Specifically, the corrected projection image is generated by subtracting the estimated scatter component computed in step 903 from an initial 2D projection image, where the initial 2D projection image is the 2D projection image that is convolved with the set of scatter-estimate kernels selected in step 902. In the first iteration of steps 903 and 904, the initial 2D projection image is the original acquired 2D projection image, and in subsequent iterations of step 903 and 904, the initial projection image is the corrected image from the preceding iteration of step 904.

It is noted that, in some embodiments, a 2D projection image can be increasingly refined via multiple iterations of steps 903-905. In such embodiments, a first-order scatter-free projection image is generated in a first iteration of steps 903-905, a second-order scatter-free projection image is generated in a second iteration of steps 903-905, a third-order scatter-free projection image is generated in a third iteration of steps 903-905, and so on. For example, in some embodiments, in the first iteration of step 903, the 2D projection image that is convolved with the set of scatter-estimate kernels is the original acquired 2D projection image, which inherently includes significant scatter signal. In subsequent iterations of step 903, the 2D projection image that is convolved with the set of scatter-estimate kernels in step 903 is a 2D projection image that has been partially refined by the removal of an estimated scatter component. That is, in subsequent iterations of step 903, a portion of scatter signal associated with the hardware-related scatter source has already been removed from the 2D projection image. Thus, in such embodiments, the estimated scatter component that is determined in later iterations of step 903 is computed based on a 2D projection image that has less scatter signal than the original acquired 2D projection image. As a result, the estimated scatter component that is determined in later iterations of step 903 is a more accurate estimate of scatter signal than the estimated scatter component that is determined in the first iteration of step 903.

In some embodiments, a first-order scatter-free projection image $I_{sf1}$ that is generated in a first iteration of steps 903-905 can be represented by Equation 1, a second-order scatter-free projection image $I_{sf2}$ that is generated in a second iteration of steps 903-905 can be represented by Equation 2, and a third-order scatter-free projection image $I_{sf3}$ that is generated in a third iteration of steps 903-905 can be represented by Equation 3:

$$I_{sf1} = I_m - (I_m \times K) \quad (1)$$

$$I_{sf2} = I_m - (I_{sf1} \times K) = I_m - [(I_m \times K) - ((I_m \times K) \times K)] \quad (2)$$

$$I_{sf3} = I_m - [(I_m \times K) - ((I_m \times K) \times K) + (((I_m \times K) \times K) \times K)] \quad (3)$$

where $I_m$ represent an acquired 2D projection image, K represents a set of scatter-estimate kernels, and $(I_m \times K)$ represents the convolution of $I_m$ with K.

In step 905, the X-ray imaging system of RT system 100 determines whether there are any remaining iterations of refinement of the 2D projection image selected in step 902. If yes, computer-implemented process 900 returns to step 903; if no, computer-implemented process 900 proceeds to step 906. In some embodiments, the number of iterations that a 2D projection image is refined (via steps 903-905) can vary depending on the particular hardware-related scatter source for which a scatter component is being determined.

For example, in such embodiments, a hardware-related scatter source that typically generates a larger scatter component in 2D projection images may be associated with a larger number of iterations (e.g., 3 or more), while a hardware-related scatter source that typically generates a smaller scatter component in 2D projection images may be associated with a smaller number of iterations (e.g., 1 or 2).

In step 906, the X-ray imaging system of RT system 100 determines whether there are any remaining 2D projection images to be selected. If yes, computer-implemented process 900 returns to step 902; if no, computer-implemented process 900 proceeds to step 907 and terminates.

In some embodiments, a scatter component for every 2D projection image in the set of 2D projection images is determined in computer-implemented method 900. In other embodiments, for computational efficiency, a scatter component for a selected fraction of the 2D projection images in the set of 2D projection images is determined in computer-implemented method 900. For example, in such embodiments, a scatter component may be determined for any sampling (e.g., one half, one quarter, one eighth, etc.) of the 2D projection images in the set of projection images. In such embodiments, scatter components for the remainder 2D projection images can be determined via interpolation. As a result, computer-implemented method 900 can be performed with sufficient speed that the scatter components for various hardware-related scatter sources can be determined and removed from a set of acquired 2D projection images in a clinical setting, for example during a treatment fraction.

In some embodiments, computer-implemented method 900 is performed after the removal of scatter caused by object 509 from the acquired 2D projection images using conventional techniques. Alternatively, in some embodiments, computer-implemented method 900 is performed prior to the removal of scatter caused by object 509 from the acquired 2D projection images. In such embodiments, the removal of object-related scatter from the acquired 2D projection images is performed using conventional techniques, but in such embodiments, the corrected images generated by computer-implemented method 900 can be employed as the input images for removal of scatter caused by object 509.

In the above embodiments, process 800 and method 900 are described with respect to a set of 2D projection images. In other embodiments, process 800 and/or method 900 can be beneficially performed on a single 2D projection image, such as a simple radiography acquisition.

Example Computing Device

Figure 10:
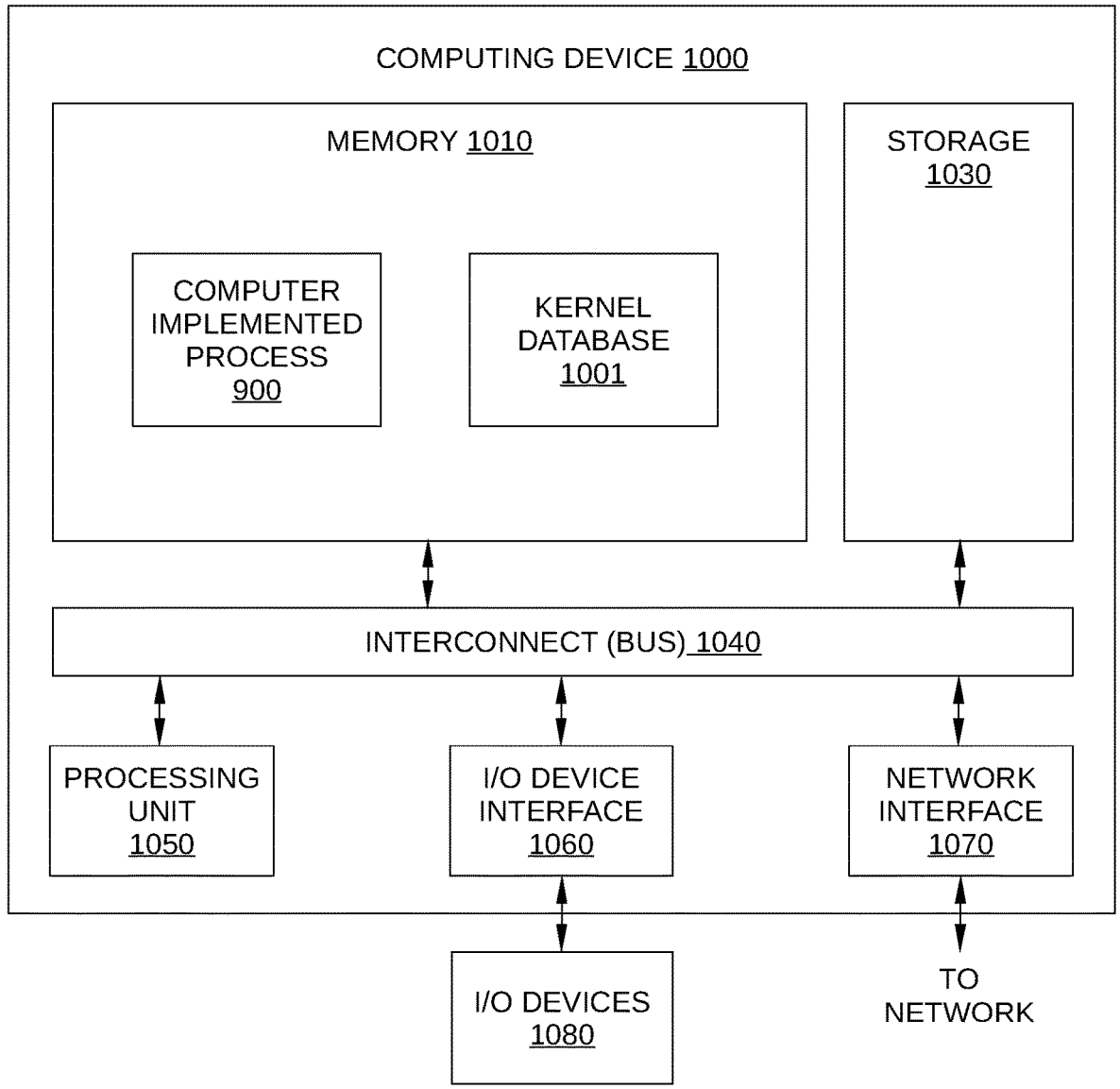
FIG. 10 is an illustration of a computing device configured to perform various embodiments.

FIG. 10 is an illustration of computing device 1000 configured to perform various embodiments of the present disclosure. For example, in some embodiments, computing device 1000 can be implemented as image acquisition and treatment control computer 106 and/or remote control console 110 in FIG. 1. Computing device 1000 may be a desktop computer, a laptop computer, a smart phone, or any other type of computing device suitable for practicing one or more embodiments of the present disclosure. In operation, computing device 1000 is configured to execute instructions associated with computer-implemented process 900, as described herein. It is noted that the computing device described herein is illustrative and that any other technically feasible configurations fall within the scope of the present disclosure.

As shown, computing device 1000 includes, without limitation, an interconnect (bus) 1040 that connects a processing unit 1050, an input/output (I/O) device interface 1060 coupled to input/output (I/O) devices 1080, memory 1010, a storage 1030, and a network interface 1070. Processing unit 1050 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1050 may be any technically feasible hardware unit capable of processing data and/or executing software applications, including computer-implemented process 900.

I/O devices 1080 may include devices capable of providing input, such as a keyboard, a mouse, a touch-sensitive screen, and so forth, as well as devices capable of providing output, such as a display device and the like. Additionally, I/O devices 1080 may include devices capable of both receiving input and providing output, such as a touchscreen, a universal serial bus (USB) port, and so forth. I/O devices 1080 may be configured to receive various types of input from an end-user of computing device 1000, and to also provide various types of output to the end-user of computing device 1000, such as displayed digital images or digital videos. In some embodiments, one or more of I/O devices 1080 are configured to couple computing device 1000 to a network.

Memory 1010 may include a random access memory (RAM) module, a flash memory unit, or any other type of memory unit or combination thereof. Processing unit 1050, I/O device interface 1060, and network interface 1070 are configured to read data from and write data to memory 1010. Memory 1010 includes various software programs that can be executed by processor 1050 and application data associated with said software programs, including computer-implemented process 900 and a kernel database 1001.

Example Computer Program Product

Figure 11:
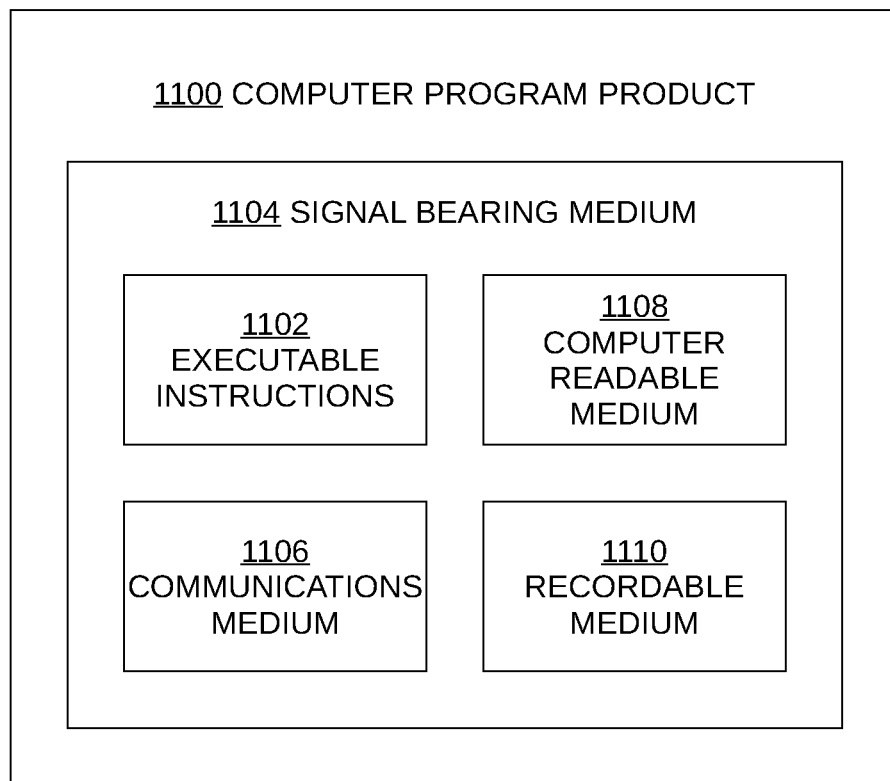
FIG. 11 is a block diagram of an illustrative embodiment of a computer program product for implementing one or more embodiments.

FIG. 11 is a block diagram of an illustrative embodiment of a computer program product 1100 for implementing a method for reducing scatter in an X-ray projection image, according to various embodiments. Computer program product 1100 may include a signal bearing medium 1104. Signal bearing medium 1104 may include one or more sets of executable instructions 1102 that, when executed by, for example, a processor of a computing device, may provide at least the functionality described above with respect to FIGS. 1-10.

In some implementations, signal bearing medium 1104 may encompass a non-transitory computer readable medium 1108, such as, but not limited to, a hard disk drive, a Compact Disc (CD), a Digital Video Disk (DVD), a digital tape, memory, etc. In some implementations, signal bearing medium 1104 may encompass a recordable medium 1110, such as, but not limited to, memory, read/write (R/W) CDs, R/W DVDs, etc. In some implementations, signal bearing medium 1104 may encompass a communication medium 1106, such as, but not limited to, a digital and/or an analog communication medium (e.g., a fiber optic cable, a waveguide, a wired communications link, a wireless communication link, etc.). Computer program product 1100 may be recorded on non-transitory computer readable medium 1108 or another similar recordable medium 1110.

In sum, embodiments described herein enable X-ray scatter that is included in a 2D projection image to be estimated and removed from the 2D projection image to produce a corrected image. In the embodiments, X-ray scatter associated with various hardware-related sources can be substantially removed, thereby improving the reconstruction quality of a digital volume that is based on the corrected image. Such improved reconstruction quality facilitates the use of CBCT-based reconstructions for treatment planning. In addition, because the embodiments enable X-ray scatter to be removed with computational efficiency, the corrected images can be employed in clinical applications, such as IGRT and/or IMRT processes.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of reducing scatter in an X-ray projection image of an object, the method comprising:
    generating an initial X-ray projection image with an imaging beam and an X-ray detector;
    based on a first position in a detector array of the X-ray detector, selecting a first kernel for convolution of a first portion of the initial X-ray projection image, wherein the first position corresponds to the first portion of the initial X-ray projection image;
    based on a second position in the detector array of the X-ray detector, selecting a second kernel for convolution of a second portion of the initial X-ray projection image, wherein the second position corresponds to the second portion of the initial X-ray projection image;
    convolving the first portion with the first kernel and the second portion with the second kernel to generate a scatter component of the initial X-ray projection image; and
    generating a corrected X-ray projection image by removing the scatter component from the initial X-ray projection image.

2. The computer-implemented method of claim 1, wherein the first kernel and the second kernel are computed prior to generating the initial X-ray projection image.

3. The computer-implemented method of claim 1, wherein selecting the first kernel is further based on a first transmission indicator associated with attenuation of the imaging beam by a first portion of the object.

4. The computer-implemented method of claim 3, wherein selecting the second kernel is further based on a second transmission indicator that is associated with attenuation of the imaging beam by a second portion of the object.

5. The computer-implemented method of claim 3, wherein the transmission indicator comprises a single value associated with a computed transmission of the imaging beam through the first portion of the object.

6. The computer-implemented method of claim 3, wherein the transmission indicator includes a measure of a selective attenuation by the object of certain frequencies included in the imaging beam.

7. The computer-implemented method of claim 3, further comprising determining the first transmission indicator of the object based on a portion of the object that is in the path of a ray that passes from an X-ray source to the first position in the detector array.

8. The computer-implemented method of claim 1, wherein each of the first kernel and the second kernel is selected based on a beam energy associated with the imaging beam.

9. The computer-implemented method of claim 1, wherein the first position comprises a first column of the detector array and the second position comprises a second column of the detector array.

10. The computer-implemented method of claim 9, wherein the first position further comprises one or more columns of the detector array that are contiguous with the first column, and the second position further comprises one or more columns of the detector array that are contiguous with the second column.

11. The computer-implemented method of claim 1, wherein the first kernel and the second kernel are included in a set of kernels, wherein each kernel in the set of kernels is associated with a different position in the detector array.

12. The computer-implemented method of claim 1, wherein the first kernel is computed analytically based on ray-tracing along a first path from the first position in the detector array to a visible portion of an anode for generating the imaging beam.

13. The computer-implemented method of claim 12, wherein the second kernel is computed analytically based on ray-tracing along a second path from the second position in the detector array to the visible portion of the anode.

14. The computer-implemented method of claim 1, wherein the first kernel and the second kernel are further selected based on an element of an imaging system that includes the X-ray detector, wherein the element is disposed on the first path and the second path.

15. The computer-implemented method of claim 14, wherein the element of the imaging system comprises one of an X-ray filter of the imaging system, a bore of the imaging system, an off-focal region of the imaging system, a detector of the imaging system, or a component of the X-ray detector.

16. The computer-implemented method of claim 1, wherein the first kernel and the second kernel are further selected based on an X-ray source of an imaging system that includes the X-ray detector.

17. The computer-implemented method of claim 1, wherein:
the detector array of the X-ray detector includes a plurality of positions; and
each position in the plurality of positions corresponds to a different portion of the initial X-ray projection image.

18. The computer-implemented method of claim 17, further comprising,
for each position in the plurality of positions, selecting a different kernel for convolution of a different corresponding portion of the initial X-ray projection image.

19. An X-ray imaging system, comprising:
an X-ray source for generating an imaging beam;
an X-ray detector; and
one or more processors configured to perform the steps of:
generating an initial X-ray projection image with the imaging beam and the X-ray detector;
based on a first position in a detector array of the X-ray detector, selecting a first kernel for convolution of a first portion of the initial X-ray projection image, wherein the first position corresponds to the first portion of the initial X-ray projection image;
based on a second position in the detector array of the X-ray detector, selecting a second kernel for convolution of a second portion of the initial X-ray projection image, wherein the second position corresponds to the second portion of the initial X-ray projection image;
convolving the first portion with the first kernel and the second portion with the second kernel to generate a scatter component of the initial X-ray projection image; and
generating a corrected X-ray projection image by removing the scatter component from the initial X-ray projection image.

20. A non-transitory computer readable medium storing instructions that, when executed by a processor, cause the processor to perform the steps of:
generating an initial X-ray projection image with an imaging beam and an X-ray detector;
based on a first position in a detector array of the X-ray detector, selecting a first kernel for convolution of a first portion of the initial X-ray projection image, wherein the first position corresponds to the first portion of the initial X-ray projection image;
based on a second position in the detector array of the X-ray detector, selecting a second kernel for convolution of a second portion of the initial X-ray projection image, wherein the second position corresponds to the second portion of the initial X-ray projection image;
convolving the first portion with the first kernel and the second portion with the second kernel to generate a scatter component of the initial X-ray projection image; and
generating a corrected X-ray projection image by removing the scatter component from the initial X-ray projection image.

* * * * *